(12) United States Patent
Fabian

(10) Patent No.: US 7,465,847 B2
(45) Date of Patent: Dec. 16, 2008

(54) RADIOPAQUE MARKER FOR A SURGICAL SPONGE

(76) Inventor: Carl E. Fabian, 577 NE. 96th St., Miami Shores, FL (US) 33138

( * ) Notice: Subject to any disclaimer, the term of this patent is extended or adjusted under 35 U.S.C. 154(b) by 340 days.

(21) Appl. No.: 10/650,376

(22) Filed: Aug. 29, 2003

(65) Prior Publication Data

US 2005/0049563 A1  Mar. 3, 2005

(51) Int. Cl.
- A61F 13/15 (2006.01)
- A61B 19/00 (2006.01)
- A61N 5/00 (2006.01)

(52) U.S. Cl. .............. 604/362; 128/899; 600/3
(58) Field of Classification Search .......... 604/362; 600/3–8; 128/899; 340/573.1
See application file for complete search history.

(56) References Cited

U.S. PATENT DOCUMENTS

| | | | | |
|---|---|---|---|---|
| 3,133,538 A | | 5/1964 | Pratt et al. | 128/296 |
| 3,736,935 A | * | 6/1973 | Reimels | 604/362 |
| 3,911,922 A | * | 10/1975 | Kliger | 604/362 |
| 3,965,907 A | | 6/1976 | Hardy et al. | 128/296 |
| 4,068,666 A | | 1/1978 | Shiff | 128/290 W |
| 4,205,680 A | * | 6/1980 | Marshall | 604/362 |
| 4,244,369 A | | 1/1981 | McAvinn et al. | 128/296 |
| 4,626,251 A | | 12/1986 | Shen | 604/362 |
| 4,639,253 A | | 1/1987 | Dyer et al. | 604/362 |
| 4,718,897 A | * | 1/1988 | Elves | 604/362 |
| 4,917,694 A | | 4/1990 | Jessup | 604/362 |
| 4,935,019 A | * | 6/1990 | Papp, Jr. | 604/362 |
| 4,938,901 A | | 7/1990 | Groitzsch et al. | 264/22 |
| 4,983,173 A | | 1/1991 | Patience et al. | 604/384 |
| 5,041,103 A | | 8/1991 | Rupinskas | 604/362 |
| 5,045,080 A | | 9/1991 | Dyer et al. | 604/362 |
| 5,112,325 A | | 5/1992 | Zachry | 604/362 |
| 5,955,776 A | * | 9/1999 | Ishikawa | 257/618 |
| 6,026,818 A | | 2/2000 | Blair et al. | 128/899 |
| 6,366,206 B1 | * | 4/2002 | Ishikawa et al. | 340/573.1 |
| 6,371,904 B1 | * | 4/2002 | Sirimanne et al. | 600/3 |
| 6,777,623 B2 | * | 8/2004 | Ballard | 177/25.13 |
| 2005/0038355 A1 | * | 2/2005 | Gellman et al. | 600/564 |

OTHER PUBLICATIONS

The Free Dictionary by Farlex; http://www.thefreedictionary.com/contiguous.*
Encarta; http://encarta.msn.com/dictionary_1861599914/contiguous.html.*
http://dict.die.net/proximate/.*
Denise Grady, "Uncommon Peril of Forgotten Surgical Tools," The New York Times, Jan. 21, 2003.

* cited by examiner

Primary Examiner—Tatyana Zalukaeva
Assistant Examiner—Michael G Bogart
(74) Attorney, Agent, or Firm—Ernest D. Buff & Associates, LLC; Ernest D. Buff; Gordon E. Fish

(57) ABSTRACT

A surgical sponge comprises a plurality of radiopaque markers having a high radiographic density and a distinctive, visually recognizable shape. The markers have an x-ray density equivalent to at least about 0.1 g/cm$^2$ of BaSO$_4$. The markers produce an x-ray image with high contrast and a shape that is readily recognizable and differentiated from the images produced by other items and structures commonly seen in x-rays of post-operative patients. Owing to the distinctive, high contrast image produced by the markers, the sponge is reliably and unambiguously detected. This is so even in situations where the sponge is inadvertently left in the surgical wound. Discomfort, trauma, and possibly fatal consequences that might otherwise occur are virtually eliminated. The surgical procedure is carried out with decreased likelihood of a sponge being retained inadvertently.

9 Claims, 4 Drawing Sheets

RADIOPAQUE MARKER FOR A SURGICAL SPONGE

BACKGROUND OF THE INVENTION

1. Field of the Invention

The present invention relates to a surgical sponge, and more particularly, to a surgical sponge or similar absorbent article having associated therewith a radiopaque marker that produces a visually distinctive shadow on an x-ray image of the sponge, rendering the sponge easily detectable and locatable within a surgical patient.

2. Description of the Prior Art

During the course of a surgical operation it is generally necessary for articles, such as surgical sponges, gauzes, instruments and the like, to be placed into a wound cavity. Sponges are often used to protect and isolate organs and tissues not directly involved in the surgical procedure; to absorb incidental blood and other bodily fluids; and to serve as aids in grasping and displacing structures to facilitate access needed to various internal regions of the patient's body.

Despite rigorous attention given to locating and removing all these items prior to completion of the surgical procedure and closure of the surgical incision, such items are sometimes overlooked and remain within the patient. When this occurs, serious consequences often ensue. The patient may suffer pain, infection, intestinal obstruction, and even death. An additional invasive surgical procedure to remove the foreign object is essential to prevent serious, and possibly fatal, consequences to the patient. A retained sponge is sometimes known in the medical literature as a "gossypiboma." In legal studies cases involving a retained surgical sponge are frequently used to illustrate the doctrine of res ipsa loquitur (the thing speaks for itself). The severity of the problem of retained surgical implements has been recognized since the earliest days of surgery. Procedures traditionally employed to prevent post-surgical implement retention include manual search of the wound by the surgeon prior to closure and a careful accounting for all materials inserted and removed from the wound. This accounting function is customarily carried out by the operating room staff, usually the circulating nurse. Notwithstanding these precautionary measures the accidental retention of surgical implements, especially sponges and the like, continues to occur to this day with disturbing regularity, even in highly respected institutions. Surgeons and related medical professionals regard this eventuality as a major unsolved problem.

At present, physical count combined with manual search remains the primary protocol used for detecting retained surgical implements. A number of difficulties compromise the efficacy of visual searching. Surgical sponges generally become soaked with blood and other bodily fluids rendering them similar in color to normal human tissues and organs. Sponges also tend to become compacted and wadded after being moistened. U.S. Pat. Nos. 4,244,369 and 4,938,901 disclose incorporation of a reflective or brightly colored fluorescent, iridescent, or phosphorescent thread in a sponge to enhance its visibility. Other sponges, such as those suggested by U.S. Pat. No. 4,068,666, are provided with a loop or locating string that may be disposed trailing out of the surgical incision.

In addition, some approaches have been proposed that would allow overlooked sponges and other surgical items to be located by remote electronic techniques and removed before completion of surgery, but these methods have not yet come into widespread use. Even with these advances, sponges are still retained. Given the serious and potentially tragic consequences that ensue, there remains a need for a redundant method of last resort, especially one that can be carried out post-surgically.

Current surgical practice employs x-ray methods for these eventualities. Most surgical instruments are composed of metal, and are relatively easily visible on x-ray. On the other hand, sponges and other non-metallic items are virtually invisible on an x-ray, so ordinarily a radiopaque component whose presence is more likely to be detected on the x-ray is securely associated with the sponge. However, intraoperative x-rays are not routinely performed before closure of the incision for several reasons: They entail the risks that inevitably arise with the extension of operative time and anesthesia, as well as undesirable expense, inconvenience, and radiation exposure. Moreover, intraoperative x-rays generally must be obtained using a portable x-ray machine. These devices generally have a lower output than fixed, standard machines, necessitating longer exposures and resulting in inferior resolution, for example due to motion of the patient which causes blurring of the image. Postoperative x-rays, even if done with a fixed machine, are still subject to some of the same disadvantages and are not routinely done unless there is a specific question or suspicion of a retained implement in a given case. Moreover, even when postoperative x-rays are obtained, retained surgical implements are still overlooked in many cases, owing to the presence of artifacts or other competing shadows on the film or the unfavorable orientation of the object relative to the x-ray incidence direction and the position of the x-ray film. The severity of the problem clearly warrants efforts that allow the aforementioned consequences to be avoided altogether by ensuring that definitive x-ray images can be obtained. It is essential that sponges be provided with a marker that may be visualized reliably and unambiguously in an x-ray image, regardless of how the sponge is handled and used during the surgical procedure. The sponge and the associated marker should not harm the patient, and should be compatible with the surgical environment and not be degraded in the presence of bodily fluids and other substances encountered during surgery.

SUMMARY OF THE INVENTION

The present invention provides a radiopaque marker suitable for association with a surgical sponge or other surgical implement. The marker has a high radiographic density and a distinctive shape, whereby the marker produces an x-ray image with high contrast and a shape that is readily recognizable and differentiated from the images produced by other items and structures commonly seen in x-rays of post-operative patients. The marker is suitable for association with a surgical sponge and has an x-ray density equivalent to at least about 0.1 g/cm$^2$ of BaSO$_4$.

In another aspect, the marker produces an x-ray image having a distinctive, visually recognizable shape. Advantageously the shape is selected from the group consisting of ovals, polygons, astroids, epicycloids, lobed shapes, alphabetic and numeric characters, and dingbats.

The invention further provides a surgical sponge comprising a radiographic marker. Such a marker has an x-ray density equivalent to at least about 0.1 g/cm$^2$ of BaSO$_4$, and a remotely detectable electronic article surveillance (EAS) tag.

The combination of the distinctive shape of the marker and its high x-ray density causes it to produce an x-ray image that much better suited to be readily and unambiguously detected than images produced by previous radiopaque elements. As a result, a sponge comprising a marker constructed in accordance with the present invention will not likely remain undetected on an x-ray if inadvertently left within a patient following a surgical procedure.

Advantageously, the presence of the EAS tag in the surgical sponge of the invention further reduces the likelihood of a sponge being retained inadvertently, since remote scanning can be carried out simply without the need of an x-ray and without risk to the patient before completion of a surgical procedure in which the sponge is used.

The invention also provides a method of detecting a surgical sponge within a surgical patient, the surgical sponge comprising a radiopaque marker having an x-ray density equivalent to at least about 0.1 $g/cm^2$ of $BaSO_4$. The method comprises the steps of: (a) obtaining at least one x-ray of at least a portion of the patient likely to contain the marker; and (b) examining the x-ray to detect and locate an image of the sponge.

BRIEF DESCRIPTION OF THE DRAWINGS

The invention will be more fully understood and further advantages will become apparent when reference is had to the following detailed description of the preferred embodiment of the invention and the accompanying drawings, in which like reference numerals denote similar items and.

DESCRIPTION OF THE PREFERRED EMBODIMENTS

The present invention provides a radiopaque marker that is adapted to be attached to a surgical sponge or surgical implement. As a result of the high radiographic density and distinctive shape of the marker, an x-ray image thereof is easily recognized. If a sponge or implement bearing such a marker is inadvertently allowed to remain within the patient after the conclusion of surgery, it may still be detected and localized by a routine postoperative x-ray and subsequently removed to prevent serious medical consequences.

Figure 1:
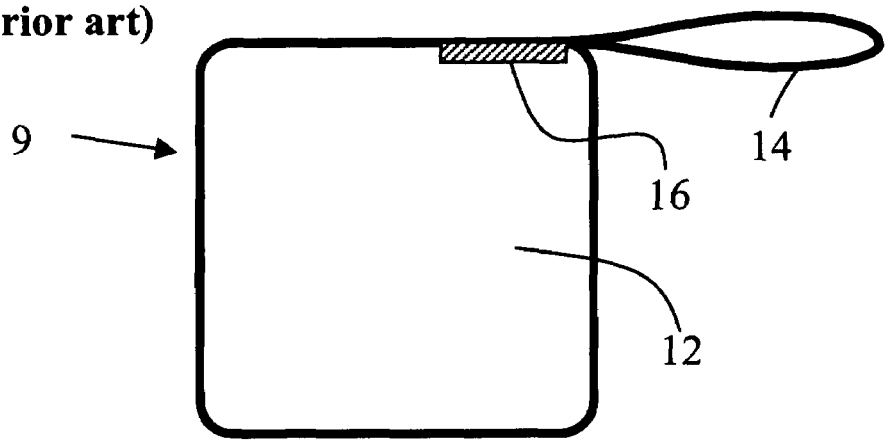
FIG. 1 is a plan view of a prior art surgical sponge including a sheet-form radiopaque element.
Figure 2:
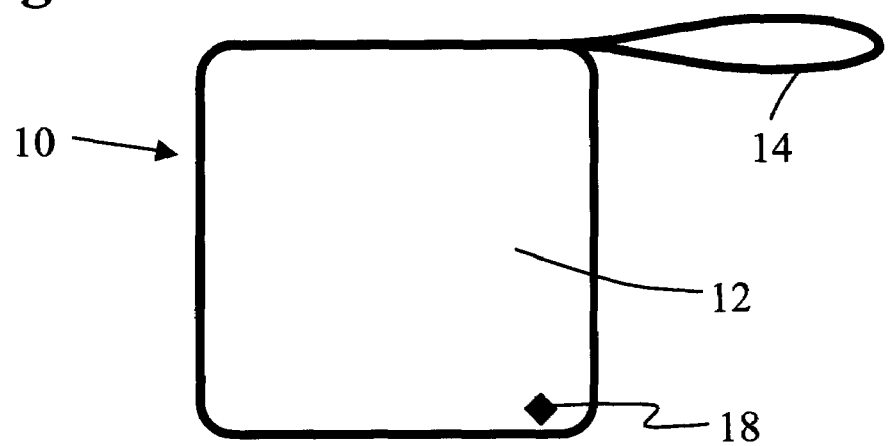
FIG. 2 is a plan view of a surgical sponge of the invention including a radiopaque marker of the invention.
Figure 3:
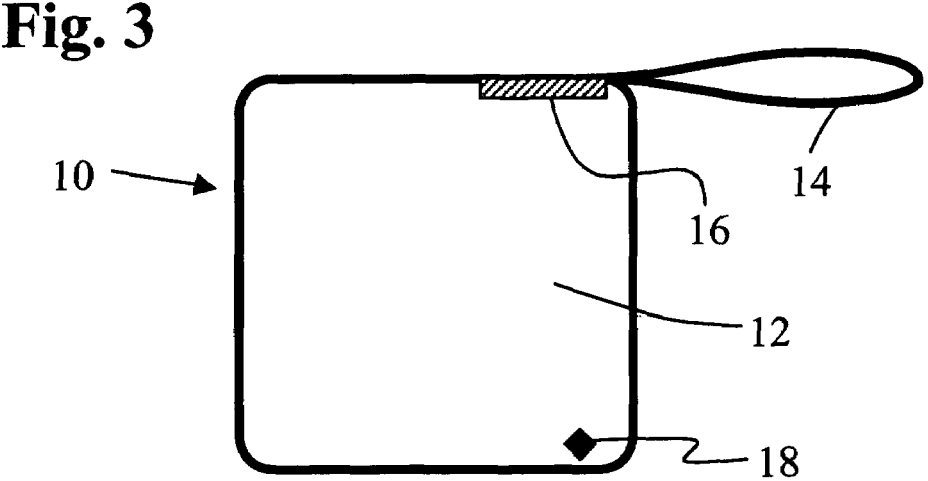
FIG. 3 is a plan view of a surgical sponge of the invention including both a sheet-form radiopaque element and a radiopaque marker of the invention.
Figure 4:
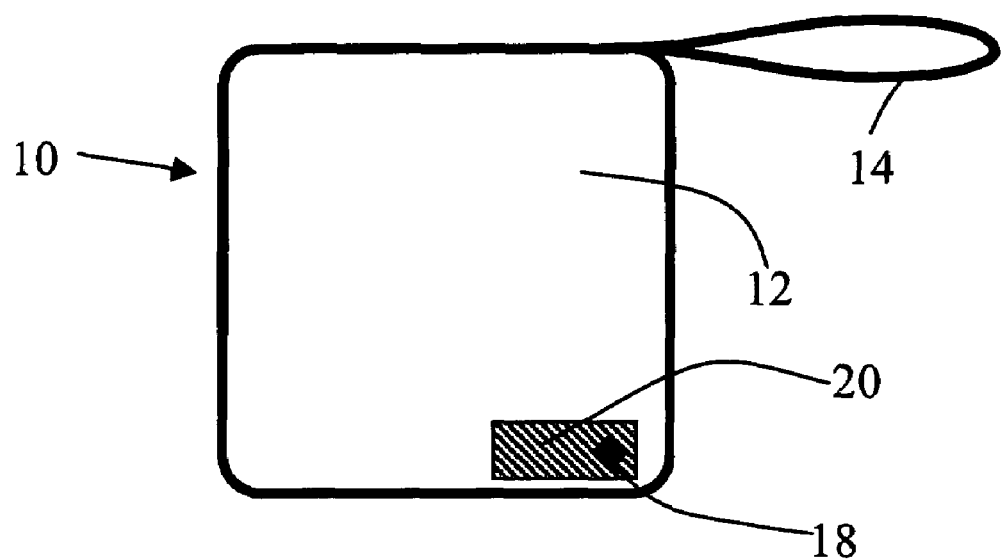
FIG. 4 is a plan view of a surgical sponge of the invention including both a radiopaque marker of the invention and an electronic article surveillance tag.
Figure 5:
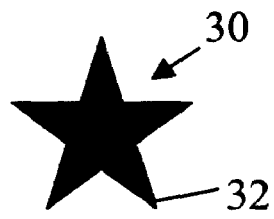
FIG. 5 is a plan view of an astroid-like radiopaque marker of the invention having five points.
Figure 6:
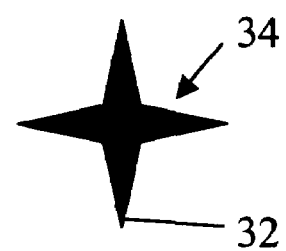
FIG. 6 is a plan view of an astroid-like radiopaque marker of the invention having four points.
Figure 7:
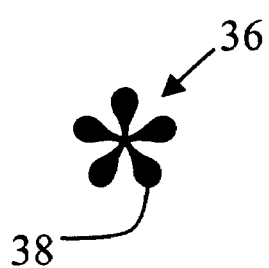
FIG. 7 is a plan view of an epicycloid-like radiopaque marker of the invention having five lobes.

Referring now to FIG. 1 there is depicted a prior art surgical sponge 9 composed of gauze 12 and having a fabric loop 14 to facilitate identification and location of the sponge. The sponge bears a generally rectangular, sheet-form radiopaque element 16. Each of FIGS. 2-4 depicts an aspect of a surgical sponge 10 of the invention. As depicted, each sponge includes an optional fabric or thread loop 14 to facilitate identification and location of the sponge. Sponge 10 further comprises a radiopaque marker 18 of the invention. A diamond-shaped marker like that of FIG. 7 is shown. However, it will be appreciated that any other form of the present marker, including, but not limited to, the forms depicted by FIGS. 5-10, may also be used in the embodiments of FIGS. 2-4. The aspect shown in FIG. 3 further includes a sheet-form radiopaque element 16 that is known in the prior art in addition to the radiographically denser marker 18.

FIG. 4 depicts a sponge 10 that further comprises a remotely detectable electronic article surveillance tag 20. The radiographic marker 18 may be attached to the surface of the housing of tag 20 as shown. Alternatively, marker 18 may be enclosed within the housing or it may be disposed separately in sponge 20. It is preferred that marker 18 be securely associated with sponge 10 in a manner that prevents it from becoming detached from sponge 10 in the course of the preparation and use of sponge 10.

The association of marker 18 with the surgical sponge 10 of the invention affords a highly reliable means of detecting sponge 10 if the sponge is used within the body of a surgical patient but inadvertently left within the patient at the completion of the surgical procedure. The marker's high radiopacity and the distinctive shape of the x-ray image it produces make its recognition significantly easier and more reliable than have been the case with prior art sponges.

A radiograph, or "x-ray image" as the term is commonly used, is obtained using a source of an incident x-ray beam and a two-dimensional, x-ray sensitive detector, most commonly being a sheet of photosensitive film. However, other forms of detection, including fluorescent screens and radiation detectors, are also widely used. The subject's body is interposed between the x-ray source and the detector. The x-ray source is activated for a predetermined time and the beam is directed at some part of the body of diagnostic interest, with the exiting beam then falling upon the detector, creating an image. The resulting image may be regarded as a shadow of the various body structures traversed by the beam before reaching the film sheet (or detector). This process, and the general nature and appearance of the image, are familiar to most persons.

Radiology can be considered the study of comparative densities of biologic tissue when exposed to x-ray and how this is used to diagnose disease. It is known that an x-ray beam becomes partially absorbed or attenuated as it passes through any object, including the human body. The degree of the attenuation depends on a number of factors, including the energy or wavelength of the incident beam, the thickness of the object traversed, and its radiodensity. Radiodensity in turn is dependent on the atomic structure of the object and more particularly on the concentration of particular atoms per volume. Atoms of higher atomic number within a tissue will therefore impart higher radiodensity to a given tissue than will atoms of lower atomic number. Furthermore, if those heavier atoms are in elemental form rather than ionized components of a chemical compound, their nuclei will in many cases be much more closely spaced together and they will therefore confer even greater radiodensity. For example, metallic iron within the body is much denser than a chemical compound of which iron is merely one component diluted by other atoms, such as hemoglobin, ferric chloride, etc. There are five broad categories of tissue density recognized on film images listed in order of decreasing radiodensity: metallic objects, bone, water, fat, and gas (or air).

A radiographic image is a pattern of lighter and darker shades and basically represents a summation shadow of all the radiodensities encountered along the path of the beam from its source to the film sheet. A dense structure along the path of the beam will attenuate or absorb the beam to a greater degree, causing the underlying portion of the film to receive less exposure by the transiting beam and generally leaving a light image on the film, and one which will obscure the image of a less dense structure along the same path. Hence metallic objects, such as bullets, shrapnel, surgical instruments, prosthetic joints, dental work, clips, and the like having a very high radiodensity will generally obscure the image of anything else of lower density along the same path, including bone, while bone in turn will tend to obscure an image of a soft tissue structure (muscle, soft tissue or fluid) along its path. Soft tissue (such as muscle, blood, fluid), absorbs x-rays to a lesser degree, so the corresponding underlying areas on the x-ray film receive more exposure and thus appear as a somewhat darker shade of gray on the film. Areas of predominantly fatty tissue attenuate less than muscle tissue and tend to appear as darker shades of gray, while the least absorbing substance, gas (or air) absorb almost none of the transiting beam and appear as shades of dark gray or black.

Other more sophisticated x-ray techniques, such as computerized axial tomography (CAT) scanning, are based on similar underlying principles. While they generally afford improved sensitivity and resolution over conventional x-rays, they are generally more costly and require greater skill both for operation and for interpretation of the resulting images. Nonetheless, the marker of the present invention may be visualized using CAT scanning and other like methods.

The preponderance of tissue in the human body is comprised of atoms of relatively low average atomic number, including hydrogen, carbon, and oxygen, nitrogen, the principal building blocks of protein. These atoms have atomic numbers of 1, 6, 8 and 7, respectively, and together comprise 96.6% of a typical adult human's body weight, [*AIP $50^{th}$ Anniversary Physics Vade Mecum,* page 212, American Institute of Physics, 1981]. These atoms are by far the most common components of fats and proteins. Moreover, much of a typical subject's body weight is in the form of water ($H_2O$), made up of atoms of hydrogen and oxygen in the ratio of 2:1. Together, proteins, fats, and water comprise most of the soft tissues of the body.

The human body also contains bones and teeth, each containing a higher concentration of heavier atoms like calcium and phosphorus (atomic numbers of 20 and 15, which typically comprise 1.4 and 1.1% of total body weight, respectively). Because of their atomic composition and calcium content, these structures are radiographically denser than soft tissues and thus create more contrast on a properly exposed x-ray, as is familiar to most persons.

For typical wavelengths used in medical radiography, bone, volume per volume, absorbs x-rays about two to four times as much as soft tissues like muscle. It is generally found that the attenuation of the intensity of an x-ray beam passing through a substance is approximately exponential with thickness. That is, the intensity I(z) of the beam after passing through a thickness "z" of the substance may be represented by the equation, $I(z)=I_0 \exp(-\mu z)$, wherein "$I_0$" is the incident intensity and $1/\mu$ is a characteristic attenuation length. The value of $\mu$ depends on several factors, which include the atomic weight of the constituent atoms and the incident x-ray wavelength.

A sample of total thickness "t" such that $\mu t$ is at least 5-10 is substantially opaque to an incident x-ray beam. In other words, the x-ray intensity incident on an object composed of such a substance is attenuated to an extent that virtually no x-rays are transmitted through the object.

A number of surgical sponges have been proposed that incorporate an element that strongly absorbs x-rays, commonly termed a radiopaque element. In principle the provision of a radiopaque element allows a sponge that is inadvertently left within a patient during a surgical procedure to be detected by means of the image it produces in a routine x-ray procedure. However, it is known that x-rays still fail in some cases to detect retained sponges. Ambiguities of the x-ray image or other factors not infrequently cause even experienced radiologists to miss a retained sponge, even if alerted by a patient's post-operative symptoms to the possibility of its presence. In addition, many of the elements in common use are not sufficiently dense to be adequately radiopaque.

Most commonly, the radiopaque elements used to mark surgical sponges are in the form of a thin sheet or a thread comprising barium sulfate ($BaSO_4$). This chemical compound is chosen as being chemically inert and non-injurious to body tissues, while containing a substantial amount of Ba, i.e. one atom of Ba per formula unit. The relatively high atomic number of Ba (56) provides it with substantial x-ray absorption. Most frequently the $BaSO_4$ is dispersed within a polymer matrix in such radiopaque elements. U.S. Pat. No. 5,112,325 discloses such a surgical sponge fabricated with a locator thread comprising $BaSO_4$-loaded monofilaments. In other cases $BaSO_4$ is deposited on a fabric element associated with the sponge. Many of the radiopaque elements currently used in connection with surgical sponges do not have a sufficient density of Ba atoms to render them adequately radiopaque. As a result, the x-ray image these elements produce is not distinct under the full range of exposure conditions commonly encountered, leading to a significant probability they will not carry out their appointed function.

It is further found that the value of $\mu$ in the aforementioned exponential equation is, to a good approximation, proportional to the mass density of the absorbing substance. As noted above, many prior art radiopaque elements comprise $BaSO_4$ in a polymeric matrix. The attendant dilution proportionately reduces the element's radiopacity. Therefore, the required thickness of the element must be increased in inverse proportion to the reduction in mass density to achieve the same radiopacity. This finding allows the radiopacity of two objects to be compared based on the respective areal mass density of the objects, that is to say, the diluted mass density of the absorbing substance times the object's thickness. The resulting value is expressed in units of $g/cm^2$ or equivalent units.

The threads and sheets used in prior art radiopaque elements are believed to have an equivalent effective thickness of $BaSO_4$ of less than about 0.2 mm, and more commonly, less than about 0.05 mm. Such elements would have an areal mass density of less than about 0.09 or 0.0225 $g/cm^2$, respectively, since BaSO4 has a density of about 4.5 $g/cm^3$. It is thus preferred that the marker of the invention have a radiographic density equivalent to at least that of an element having about 0.1 $g/cm^2$ of $BaSO_4$ and more preferably at least about 0.2 $g/cm^2$ of $BaSO_4$.

Figure 11:
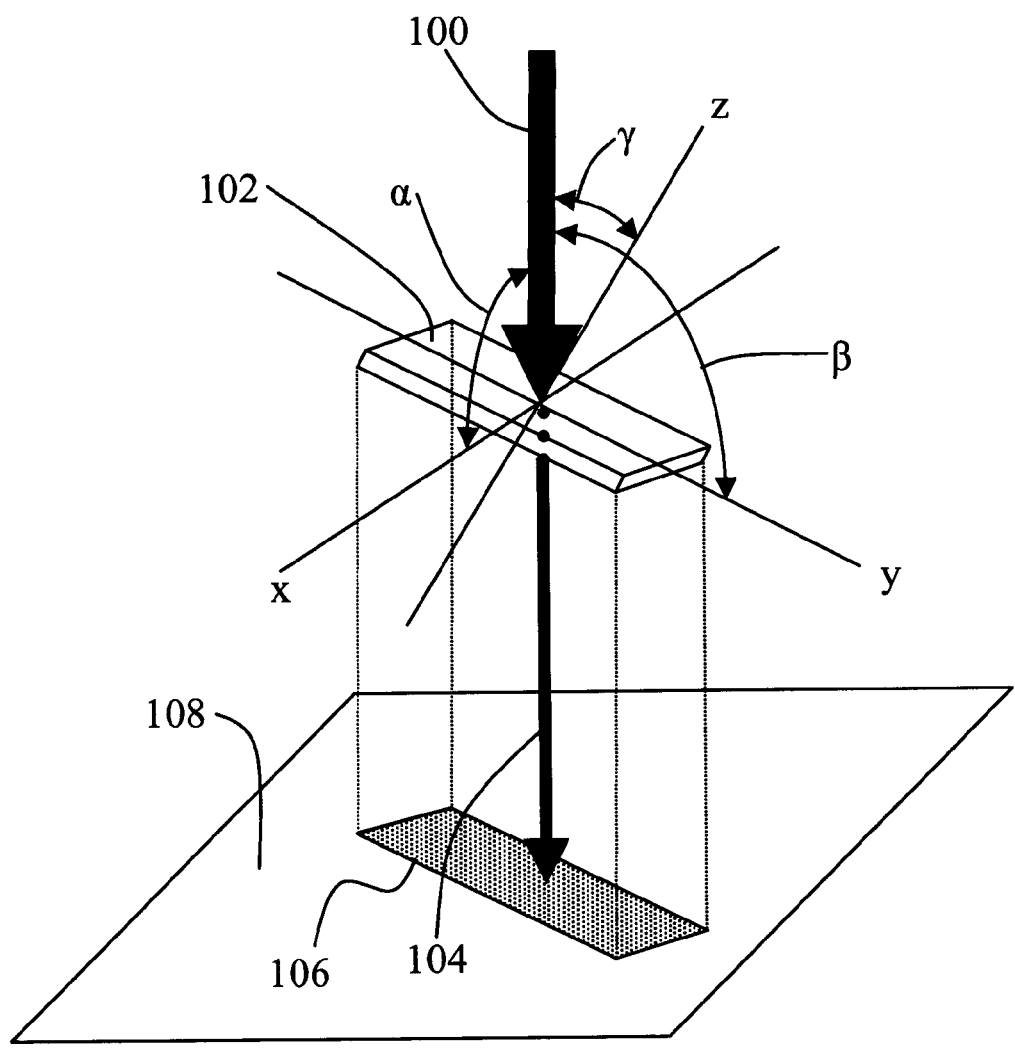
FIG. 11 is a perspective view depicting a marker oriented obliquely to an incident x-ray beam and the resulting shadow image on an x-ray film.

The x-ray image of a radiopaque object is a two-dimensional shadow projection. That is, the exposure of the x-ray at each point of the image reflects the total x-ray density along a path connecting the x-ray source and the point. Both the effective x-ray density and the apparent shape of the projection of the object are a consequence of the relative orientation of the object and the incident beam direction. FIG. 11 depicts the simple case of an x-ray beam 100 incident on a rectangular, sheet-form element 102 with uniform x-ray density. An attenuated beam 104 emerges below element 102 and creates a projected shadow image 106, i.e., a region of reduced exposure on x-ray film 108. The beam 100 is oriented at angles α, β, and γ relative to the x, y, and z axes, respectively, of a Cartesian coordinate system having the z axis perpendicular to the element's planar surface and the x and y axes in the plane. The effective thickness of the element 102 in this orientation is increased by a factor $[1/\cos(\gamma)]$, in which $\cos(\gamma)$ is the cosine of the angle γ. The image 106 of the element 104 is foreshortened in the x-direction by a factor $\cos(\alpha)$ and in the y-direction by a factor $\cos(\beta)$. Consequently, the apparent image 106 of the element may shrink considerably if the beam is incident on the element in a direction far from normal, making it much more difficult to recognize. It will readily be apparent that a retained sponge may be located at any orientation within a patient's body and thus subject to the foregoing considerations.

A further complication in detecting prior art sponges arises from the manner in which the sponges are commonly folded or wadded in the course of surgery. These actions frequently cause the shape of an attached radiopaque element to be substantially deformed from its initial conformation. The resulting shadow of the radiopaque element that is projected on the x-ray may thus take on a shape that is unpredictable and unexpected, leading to a markedly higher chance of the element going unrecognized, even by a trained radiologist or other observer prompted to look for the element.

Still another complication is that the radiopaque element may be located in close proximity to another radiographically dense object. The element may be positioned along an x-ray path intercepting a bone or other dense body structure so that its shadow is obscured by the superimposed denser object. More importantly, a variety of objects may intentionally be left post-operatively within a patient, including sutures, staples, catheters, implantable electronic devices such as cardiac pacemakers and defibrillators with associated wires and batteries, and prosthetic joints and other similar orthopedic hardware. Many of these devices contain substantial metal or other heavy atom content. Some of these items may produce an x-ray image that is confusingly similar to that of a marked sponge. In many cases, there are also foreign items unavoidably present within a patient's body. For example, it is often impossible or inadvisable to remove every metallic item or fragment from a patient victimized by a gunshot or other trauma. All of the aforementioned items are likely to have an x-ray density sufficient to produce discernable images in a conventional x-ray that confound attempts to identify retained surgical implements, even those provided with conventional radiopaque elements.

The radiopaque marker of the present invention has a shape that markedly enhances its detectability by x-ray techniques. Many prior art radiopaque elements have a simple one- or two-dimensional shape. For example, one or more elongated threads comprising a radiographically dense material have been used as a radiopaque element in a surgical sponge. Such an element produces a one-dimensional x-ray image, i.e., a straight or curved line segment of lessened exposure. Even if the resulting x-ray shadow image exhibits high contrast, it is likely to be confused with images produced by other elongated objects such as sutures, staples, wires, and catheters that are also expected in a surgical patient. Other sponges are marked with a rectangular, two-dimensional element. Such an element also produces a two-dimensional image, i.e. an extended area of lessened exposure that in some cases is not easily differentiated from other artifacts.

The present marker incorporates a radiopaque component adapted to produce an x-ray image having a distinctive shape.

Figure 8:
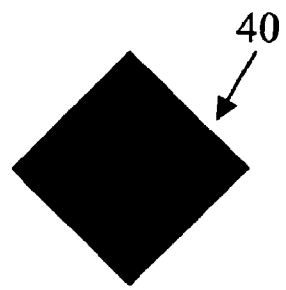
FIG. 8 is a plan view of a diamond-shaped radiopaque marker of the invention having five points.
Figure 9:
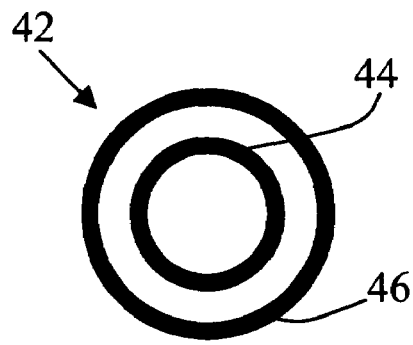
FIG. 9 is a plan view of a radiopaque marker of the invention having a bullseye-like shape

As used herein, the term "distinctive shape" means a shape that is not similar to that of items that are otherwise present in the body of a post-surgical patient. A wide variety of such shapes are suitable for incorporation in the marker of the invention, including, but not limited to, ovals including circles and ellipses, polygons; astroids, epicycloids, and similar lobed shapes; shapes approximating those of ordinary alphabetic and numeric characters and typographic symbols known in the graphic arts and printing trades as dingbats. A number of these shapes are depicted by FIGS. 5-10. An astroid-like or star-like shape, which has a plurality of pointed vertices 32 at its periphery, is seen in each of FIGS. 5 and 6, which depict a five-pointed star 30 and a four-pointed star 34, respectively. An epicycloid-like shape has a plurality of rounded lobes at its periphery. FIG. 7 depicts an epicycloid structure 36 similar to a typographic asterisk symbol and having five lobes 38. FIG. 8 depicts a polygonal structure, in particular a four-sided diamond 40. FIG. 9 depicts a bullseye-like structure comprising two concentric rings of radiopaque material. Other geometric shapes will suggest themselves to one of ordinary skill and are useful in the practice of the present invention. Included are various geometric shapes similar to the shapes of dingbats, that is, decorative or ornamental typographical characters.

Figure 10:
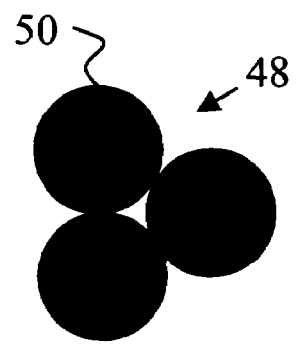
FIG. 10 is a plan view of a radiopaque marker of the invention comprising a plurality of spherical components.

In a preferred aspect marker 18 comprises a plurality of components having the same or different shapes. The presence of such shapes in a marker, in a known combination, further enhances the likelihood that an x-ray image of the marker will be recognized by a radiologist examining the x-ray. It is more preferred that the plurality of shapes be disposed in a relationship that is substantially fixed both in spacing and in orientation. Such a marker 48, as depicted by FIG. 10, comprises a plurality of closely proximate or contiguous spheres 50. Other similar markers will suggest themselves to the skilled person and are understood to be within the scope of the present invention.

A radiographic marker comprising at least one spherically shaped component advantageously produces a distinct image regardless of the relative orientation of the component and the incident x-ray beam. Symmetry considerations provide that a spherical component will produce an image having both the same size and the same radiographic density for any direction of the incident beam. A marker comprising at least one spherically-shaped component is thus far less prone to the producing the ambiguous images that result, for example, from a sheet-form element that is folded or wadded during the use of the sponge to which it is attached. Other marker components that have substantial radiographic thickness in each of the Cartesian directions, e.g., a rectangular prism or cube, also produce distinct images for any direction of beam incidence, although the image may change shape to some extent. Markers comprising at least one such component having substantial radiographic thickness in each Cartesian direction are thus within the scope of this preferred embodiment of the invention.

The radiopaque marker of the invention also has an area of at least about 5 mm$^2$ to assure that it provides an x-ray shadow large enough to be readily recognizable in a conventional x-ray. As discussed hereinabove in more detail, the effective area of a planar element is reduced if the x-ray beam is incident on the sample in a direction far from normal. Accordingly, it is preferred that the marker comprise components having a significant thickness in three dimensions. That is to say, it is preferred that the marker have an effective are of at least 5 mm$^2$ for an x-ray beam incident on the marker in any direction. Such an area is easily achieved, for example, using a marker comprising a plurality of substantially spherical components, such as that depicted by FIG. 10.

It is still further preferred that the marker of the invention has, in combination, a high radiographic density and a high effective area for an x-ray beam incident thereon at any orientation.

In a further aspect of the invention depicted by FIG. 4, a surgical sponge comprises in combination a radiographic marker and a remotely detectable electronic article surveillance tag. Such a sponge advantageously may be detected by the electronic means and removed from the patient prior to completion of surgery. However, even if the sponge is inadvertently not detected and removed, the marker further enhances the detectability of the present sponge in comparison to sponges bearing previously known radiopaque elements.

The marked surgical sponge of the invention may be used in conjunction with any EAS system capable of sensing and remotely detecting an EAS tag and compatible with the requirements of safe operation in the context of a medical venue. A wide variety of such EAS systems are currently known, including microwave, RF, and magnetic systems. Some of these systems employ substantially identical tags, so that the system simply indicates the presence or absence of a tag. Other systems have now become available in which each tag has a unique signature that is remotely recognizable by the detection system. One such system is the magneto-mechanically actuated article surveillance system disclosed by U.S. Pat. Nos. 4,510,489 and 4,510,490. Another system is the harmonic-responsive article surveillance system disclosed by U.S. Pat. No. Re. 35,042.

Many tags suitable for use in the practice of the present invention comprise an active electronic receptor element that is encased in a plastic housing comprising some means allowing the tag to be attached to another item. The term "tag" is used herein to refer generically to the combination of the active element and any housing or related mounting means. In addition, it will be understood that a tag may include more than one active element, which elements may be responsive to EAS systems of different types. It will also be appreciated that more than one tag may be attached to a given surgical item to further improve its detectability or to allow detection by EAS systems of different types.

Having thus described the invention in rather full detail, it will be understood that such detail need not be strictly adhered to but that various changes and modifications may suggest themselves to one skilled in the art, all falling within the scope of the invention as defined by the subjoined claims.

What is claimed is:

1. A surgical sponge comprising:
   a) three substantially spherical radiopaque markers;
   b) all three of said markers being closely grouped, proximate and directly contiguous to one another;
   c) each of said markers having an x-ray density equivalent to at least about 0.1 g/cm$^2$ of BaSO$_4$; and
   d) said radiopaque markers being disposed in a relationship that is substantially fixed both in spacing and in orientation, whereby said markers produce an x-ray image having a distinctive, visually recognizable shape.

2. A surgical sponge as recited by claim 1, wherein each of said markers has an x-ray density equivalent to at least about 0.1 g/cm$^2$ of BaSO$_4$ for x-rays incident on said target in any direction.

3. A surgical sponge as recited by claim 1, wherein said x-ray density is equivalent to at least about 0.2 g/cm$^2$ of BaSO$_4$.

4. A surgical sponge as recited by claim 2, wherein said x-ray density is equivalent to at least about 0.2 g/cm$^2$ of BaSO$_4$.

5. A surgical sponge as recited by claim 1, wherein each of said markers has an area of at least 5 mm$^2$ in at least one projection.

6. A surgical sponge as recited by claim 5, wherein each of said markers has an area of at least 5 mm$^2$ in any projection.

7. A surgical sponge as recited by claim 1, further comprising a remotely detectable electronic article surveillance tag.

8. A method of detecting a surgical sponge within a surgical patient, said surgical sponge comprising three substantially spherical radiopaque markers, all three of said markers being closely grouped, proximate and directly contiguous to one another, each of said markers having an x-ray density equivalent to at least about 0.1 g/cm$^2$ of BaSO$_4$, said radiopaque markers being disposed in a relationship that is substantially fixed both in spacing and in orientation, whereby said markers produce an x-ray image having a distinctive, visually recognizable shape, and said method comprising the steps of:
   (a) obtaining at least one x-ray of at least a portion of said patient likely to contain said radiopaque markers; and
   (b) examining said x-ray to detect and locate an image of said sponge.

9. A method of detecting a surgical sponge within a surgical patient and treating said surgical patient, said surgical sponge comprising three substantially spherical radiopaque markers, all three of said markers being closely grouped, proximate and directly contiguous to one another, each of said markers having an x-ray density equivalent to at least about 0.1 g/cm$^2$ of BaSO$_4$, said radiopaque markers being disposed in a relationship that is substantially fixed both in spacing and in orientation, whereby said markers produce an x-ray image having a distinctive,
visually recognizable shape, and said method comprising the steps of:
   (a) obtaining at least one x-ray of at least a portion of said patient likely to contain said radiopaque markers;
   (b) examining said x-ray to detect and locate an image of said sponge; and
   (c) carrying out a surgical procedure to remove said sponge from said patient.

* * * * *